(12) United States Patent
Andoh

(10) Patent No.: US 10,436,695 B2
(45) Date of Patent: Oct. 8, 2019

(54) PARTICULATE MATTER DETECTION SYSTEM

(71) Applicant: DENSO CORPORATION, Kariya, Aichi-pref. (JP)

(72) Inventor: Kouji Andoh, Kariya (JP)

(73) Assignee: DENSO CORPORATION, Kariya (JP)

(*) Notice: Subject to any disclaimer, the term of this patent is extended or adjusted under 35 U.S.C. 154(b) by 117 days.

(21) Appl. No.: 15/740,845

(22) PCT Filed: May 13, 2016

(86) PCT No.: PCT/JP2016/064298
§ 371 (c)(1),
(2) Date: Dec. 29, 2017

(87) PCT Pub. No.: WO2017/002462
PCT Pub. Date: Jan. 5, 2017

(65) Prior Publication Data
US 2018/0195947 A1    Jul. 12, 2018

(30) Foreign Application Priority Data
Jun. 30, 2015   (JP) .................. 2015-131416

(51) Int. Cl.
*G01N 15/06* (2006.01)
*G01N 27/04* (2006.01)
*F02D 41/14* (2006.01)
*F02D 41/20* (2006.01)
*G01N 15/00* (2006.01)

(52) U.S. Cl.
CPC ...... *G01N 15/0656* (2013.01); *F02D 41/1444* (2013.01); *F02D 41/1494* (2013.01); *G01N 15/0606* (2013.01); *G01N 27/04* (2013.01); *F01N 2560/05* (2013.01); *F01N 2560/20* (2013.01); *F02D 2041/2058* (2013.01); *G01N 2015/0046* (2013.01)

(58) Field of Classification Search
CPC .......... G01N 15/0656; G01N 15/0606; G01N 27/04; G01N 2015/0046; F02D 41/1444; F02D 41/1494; F02D 2041/2058; F01N 2560/20; F01N 2560/05
USPC ........................................ 73/25.05
See application file for complete search history.

(56) References Cited

U.S. PATENT DOCUMENTS 8,640,526 B2 * 2/2014 Di Miro ............ F02D 41/1466
324/693
2011/0314899 A1  12/2011 Di Miro et al.
(Continued)

*Primary Examiner* — Marrit Eyassu
(74) *Attorney, Agent, or Firm* — Nixon & Vanderhye P.C.

(57) ABSTRACT

A particulate matter detection system has a particulate matter detection sensor, a current detection part and a control circuit part. The particulate matter detection sensor has an accumulation part, a pair of electrodes and a heater part. The control circuit part performs switching of a detection mode and a burning mode. When the burning mode being switched to the detection mode, the control circuit part supplies a lower voltage between the pair of electrodes, which is lower than an usual voltage used in the detection mode, and detects a current detected by the current detection part as the offset value ΔI. In the detection mode, the control circuit part subtracts the offset value ΔI from the detected current value to correct the detected current value.

5 Claims, 13 Drawing Sheets

(56) References Cited

U.S. PATENT DOCUMENTS

2012/0031169 A1* 2/2012 Sakamoto ........... F02D 41/1466
73/25.05
2012/0103059 A1* 5/2012 Kimata ................ F01N 11/00
73/23.33
2012/0247181 A1* 10/2012 Nishijima .......... G01N 15/0656
73/23.33

* cited by examiner

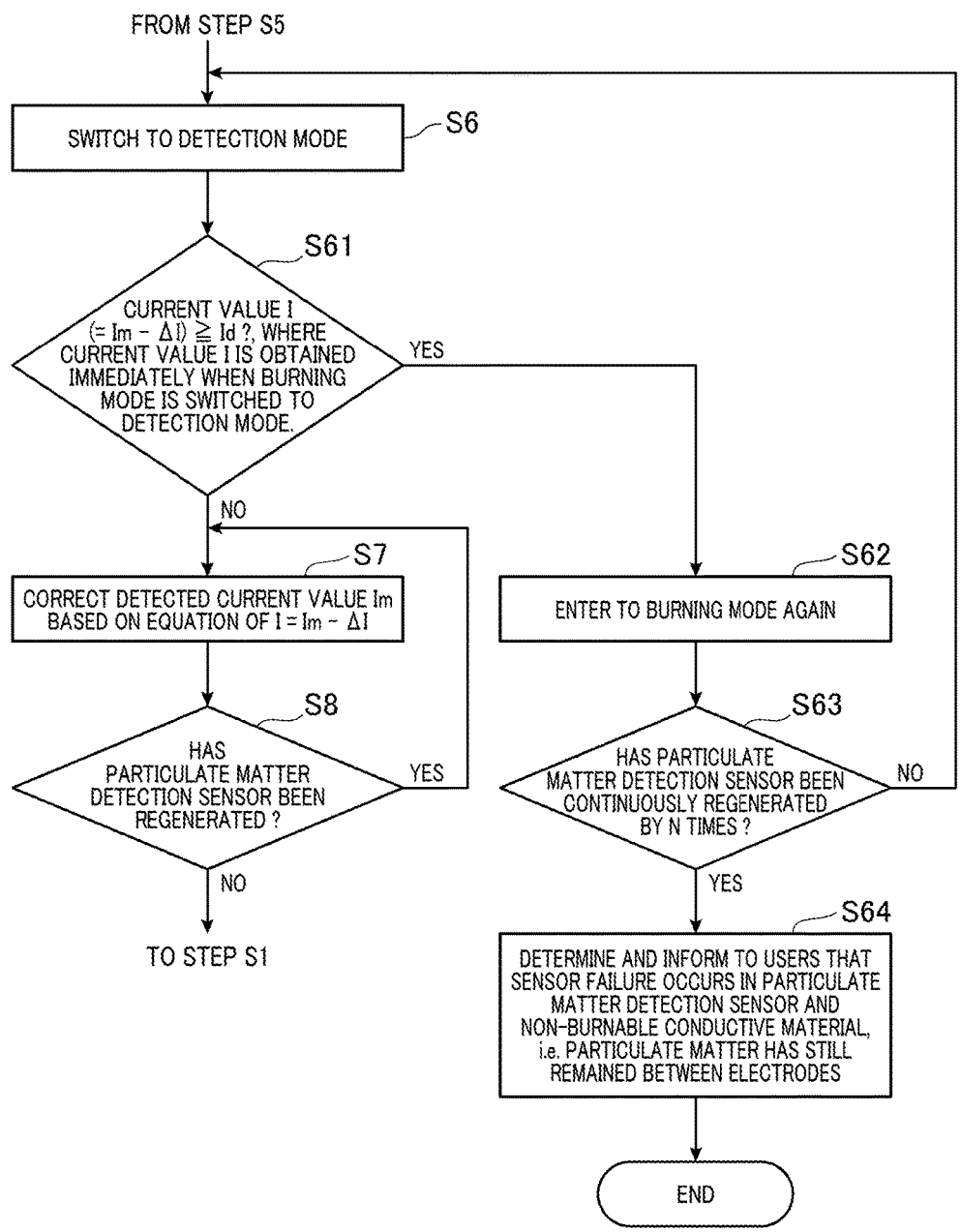

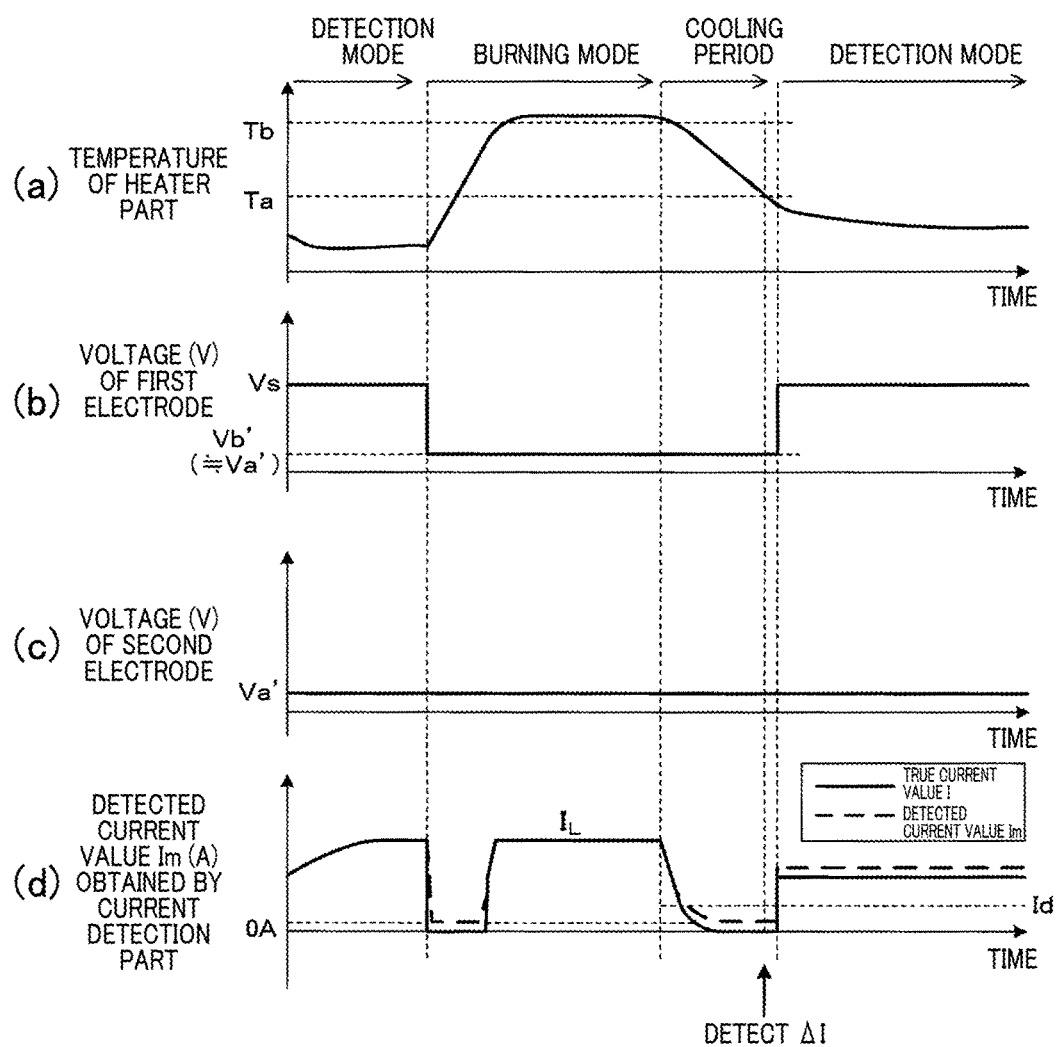

PARTICULATE MATTER DETECTION SYSTEM

This application is the U.S. national phase of International Application No. PCT/JP2016/064298 filed May 13, 2016 which designated the U.S. and claims priority to JP Patent Application No. 2015-131416 filed Jun. 30, 2015, the entire contents of each of which are hereby incorporated by reference.

TECHNICAL FIELD

The present invention relates to particulate matter detection sensors measuring an amount of particulate matter contained in exhaust gas, and also relates to particulate matter detection systems equipped with a current detection part connected to the particulate matter detection sensor, and a control circuit connected to the particulate matter detection sensor and the current detection part.

BACKGROUND ART

A particulate matter detection system is known, which is equipped with a particulate matter (PM) detection sensor, a current detection part connected to the particulate matter detection sensor and a control circuit connected to the particulate matter detection sensor and the current detection part. For example, Patent document 1 discloses a conventional particulate matter detection system. The particulate matter detection sensor has a pair of electrodes and a heater for heating the electrodes.

The control circuit is configured to perform a switching control of a detection mode and a burning mode. In the detection mode, a voltage is supplied between the pair of electrodes in the particulate matter detection sensor. In the detection mode, particulate matter is collected and accumulated between the pair of electrodes by electrostatic force and a current flows between the pair of electrodes due to the accumulation of particulate matter. The current detection part detects the current, and the control circuit part calculates an amount of particulate matter on the basis of the detected current.

Particulate matter is collected between the electrodes after long execution of the detection mode. As a result, the current flowing between the electrodes becomes saturated. After the saturation of the current flowing between the electrodes, the control circuit switches to the burning mode from the detection mode, and burns the accumulated particulate matter so as to remove the accumulated particulate matter from the particulate matter detection sensor. This regenerates the particulate matter detection sensor.

The current detection part is composed of a plurality of electronic components such as operational amplifiers, etc. Each of the electronic components varies electrical characteristics thereof due to a temperature, etc. For this reason, there is in general a difference (i.e. an offset value) between a current value detected by the current detection part and a correct current value which is proportional to an amount of particulate matter accumulated between the electrodes. Accordingly, an incorrect amount of particulate matter contained in exhaust gas is often calculated due to only using the current value detected by the current detection part.

In order to avoid this problem and to accurately detect an amount of particulate matter contained in exhaust gas, there has been proposed a method of correcting the current value detected by the current detection part, and of calculating an accurate current value flowing between the pair of electrodes on the basis of the corrected current value. That is, after the burning mode and before starting of the detection mode, the current detection part detects a current flowing between the pair of electrodes, and stores the detected current value as an offset value into a memory. When particulate matter accumulated between the pair of electrodes has been burned completely, no current flows between the pair of electrodes. Accordingly, it is possible to consider that the detected current value obtained by the current detection part is substantially equal to the offset value. It is therefore possible to detect a true current value flowing between the pair of electrodes and to accurately detect an amount of particulate matter contained in exhaust gas by subtracting the offset value from the detected current value obtained in the detection mode.

CITATION LIST

Patent Literature

[Patent document 1] Japanese patent laid open publication No. JP 2012-37373.

SUMMARY OF INVENTION

Technical Problem

However, there is a possible case for the conventional particulate matter detection system having the structure previously described to be difficult to accurately detect an amount of particulate matter contained in exhaust gas. That is, the burning mode does not completely remove the accumulated particulate matter, and as a result some amount of particulate matter are remained between the pair of electrodes. In the conventional particulate matter detection system having the structure previously described, because a high voltage is also supplied between the pair of electrodes after the burning mode is finished, similar to the detection mode, a current flows between the pair of electrodes, and this prevents the offset value from being accurately obtained. Accordingly, it is difficult to detect an accurate current value flowing between the pair of electrodes on the basis of the incorrect offset value, and to accurately detect the amount of particulate matter contained in exhaust gas.

The present invention has been made in consideration of the foregoing circumstances, and it is an object of the present invention to provide a particulate matter detection system capable of accurately detecting an amount of particulate matter contained in exhaust gas.

Solution to Problem

In accordance with one aspect of the present invention, there is provided a particulate matter detection system having a particulate matter detection sensor, a current detection part and a control circuit part. The particulate matter detection sensor has an accumulation part, a pair of electrodes and a heater part. Particulate matter contained in exhaust gas is accumulated on the accumulation part. The pair of electrodes are arranged to be separated from each other on the accumulation part. The heater part generates heat energy to heat the accumulation part. In the particulate matter detection system, the current detection part is electrically connected to one of the pair of electrodes. The control circuit part is electrically connected to the particulate matter detection sensor and the current detection part. The control circuit part performs switching of a detection mode and a burning mode. In the detection mode, the control circuit part prohibits supply of power to the heater part, supplies a voltage to the pair of electrodes, and instructs the current detection part to detect a current flowing between the pair of electrodes. In the burning mode, the control circuit part instructs the heater part to generate heat energy so as to burn particulate matter accumulated between the pair of electrodes. When switching from the burning mode to the detection mode, the control circuit part supplies, to the pair of electrodes, a second voltage which is lower than a first voltage supplied between the pair of electrodes in the detection mode. The control circuit part calculates, as an offset value, a difference between a true current value and a detected current value detected by the current detection part. In the detection mode, the control circuit part subtracts the offset value from the detected current value so as to correct the detected current value.

Advantageous Effects of Invention

When switching from the burning mode to the detection mode, the control circuit part in the particulate matter detection system supplies, to the pair of electrodes, a voltage which is lower than a voltage to be supplied to the pair of electrodes in the detection mode. At this time, the control circuit part detects, as the offset value, the output from the current detection part. It is possible to prohibit a current from flowing between the pair of electrodes when the voltage, which is lower than the voltage used in the detection mode, is supplied between the pair of electrodes when the burning mode is switched to the detection mode even if some amount of particulate matter remains between the pair of electrodes due to insufficient burning. Although varying due to the characteristics of the control circuit part produced by the manufacturing, this voltage, to be supplied to the pair of electrode when the burning mode is switched to the detection mode and which is lower than the usual voltage to be supplied to the pair of electrode in the detection mode, is a voltage with which no current flows between the pair of electrodes even if some particulate matter has remained between the pair of electrodes due to insufficient burning. That is, even if some particulate matter has remained between the pair of electrodes 21, it is possible to prevent a current from flowing between the pair of electrodes 21 with a low voltage. This low voltage is lower than the usual voltage used in the detection mode, and by which no current flows between the pair of electrodes when the burning mode is switched to the detection mode.

Because the output value of the current detection part at this time is substantially equal to the offset value, it is possible to obtain an accuracy offset value. Accordingly, it is possible for the control circuit part to obtain the true current value flowing between the pair of electrodes with high accuracy, which does not include the offset value, by subtracting the obtained offset value from the current value detected by the current detection part. The true current value corresponds to the amount of particulate matter accumulated between the pair of electrodes. This makes it possible to calculate the amount of particulate matter contained in exhaust gas with high accuracy.

As previously described, the present invention can provide the particulate matter detection system capable of detecting an amount of particulate matter contained in exhaust gas with high accuracy.

BRIEF DESCRIPTION OF DRAWINGS

FIG. 13 is view showing a part of the flow chart of the control circuit part in the particulate matter detection system according to a sixth exemplary embodiment of the present invention.

FIG. 14 is a diagram showing various graphs, (a) is a graph showing a temperature of the heater part, (b) is a graph showing a voltage potential of the first electrode, (c) is a graph showing a voltage potential of the second electrode, and (d) is a graph showing a time change of a current value detected by the current detection part when some particulate matter are remained between the first and second electrodes due to insufficient burning in the particulate matter detection system according to the sixth exemplary embodiment of the present invention.

DESCRIPTION OF EMBODIMENTS

Next, a description will be given of the in the particulate matter detection system as one aspect of the present invention, which is mounted on a diesel vehicle, capable of detecting particulate matter contained in exhaust gas emitted from a diesel engine of such a diesel vehicle. The particulate matter detection system according to the present invention can be applied to various systems and internal combustion engines emitting particulate matter.

EXEMPLARY EMBODIMENTS (First Exemplary Embodiment)

A description will be given of the particulate matter detection system according to the first exemplary embodiment with reference to FIG. 1 to FIG. 8.

Figure 4:
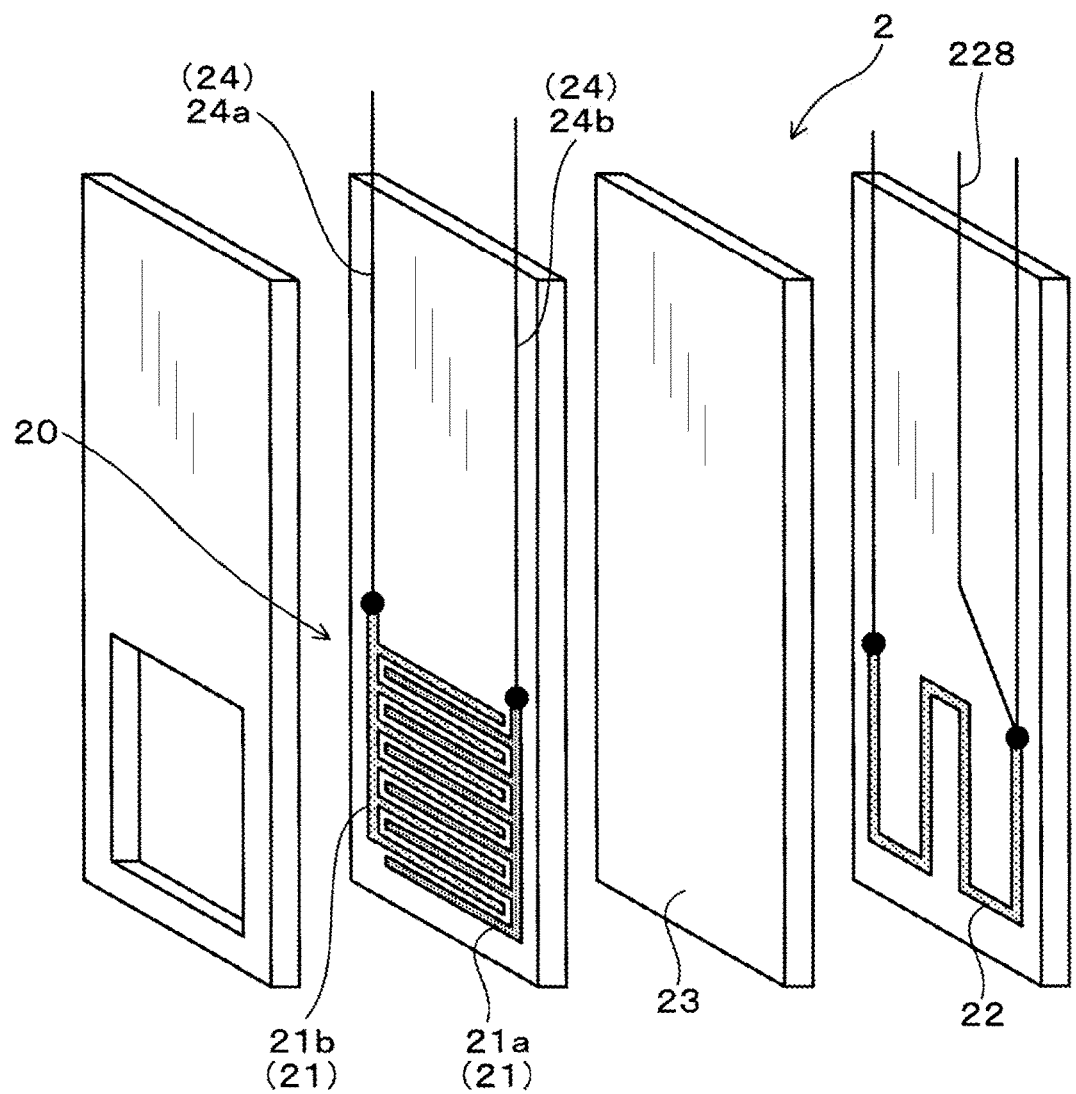
FIG. 4 is a perspective exploded view showing a particulate matter detection sensor in the articulate matter detection system according to the first exemplary embodiment of the present invention.
Figure 8:
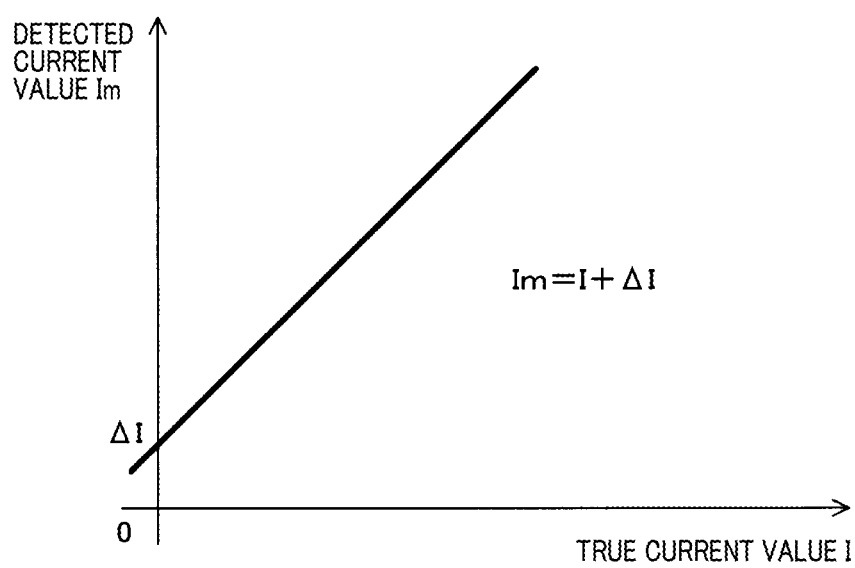
FIG. 8 is a graph showing a relationship between a detected current value and a true current value in the particulate matter detection system according to the first exemplary embodiment of the present invention.

As shown in FIG. 8, the particulate matter detection system 1 according to the first exemplary embodiment has a particulate matter detection sensor 2, a current detection part 3, and a control circuit part 4. As shown in FIG. 4, the particulate matter detection sensor 2 has an accumulation part 20, a pair of electrodes 21, and a heater part 22. Particulate matter is accumulated on the accumulation part 20. The pair of electrodes 21 are formed and arranged to separate from each other on the accumulation part 20. The heater part 22 generates heat energy to heat the accumulation part 20.

Figure 1:
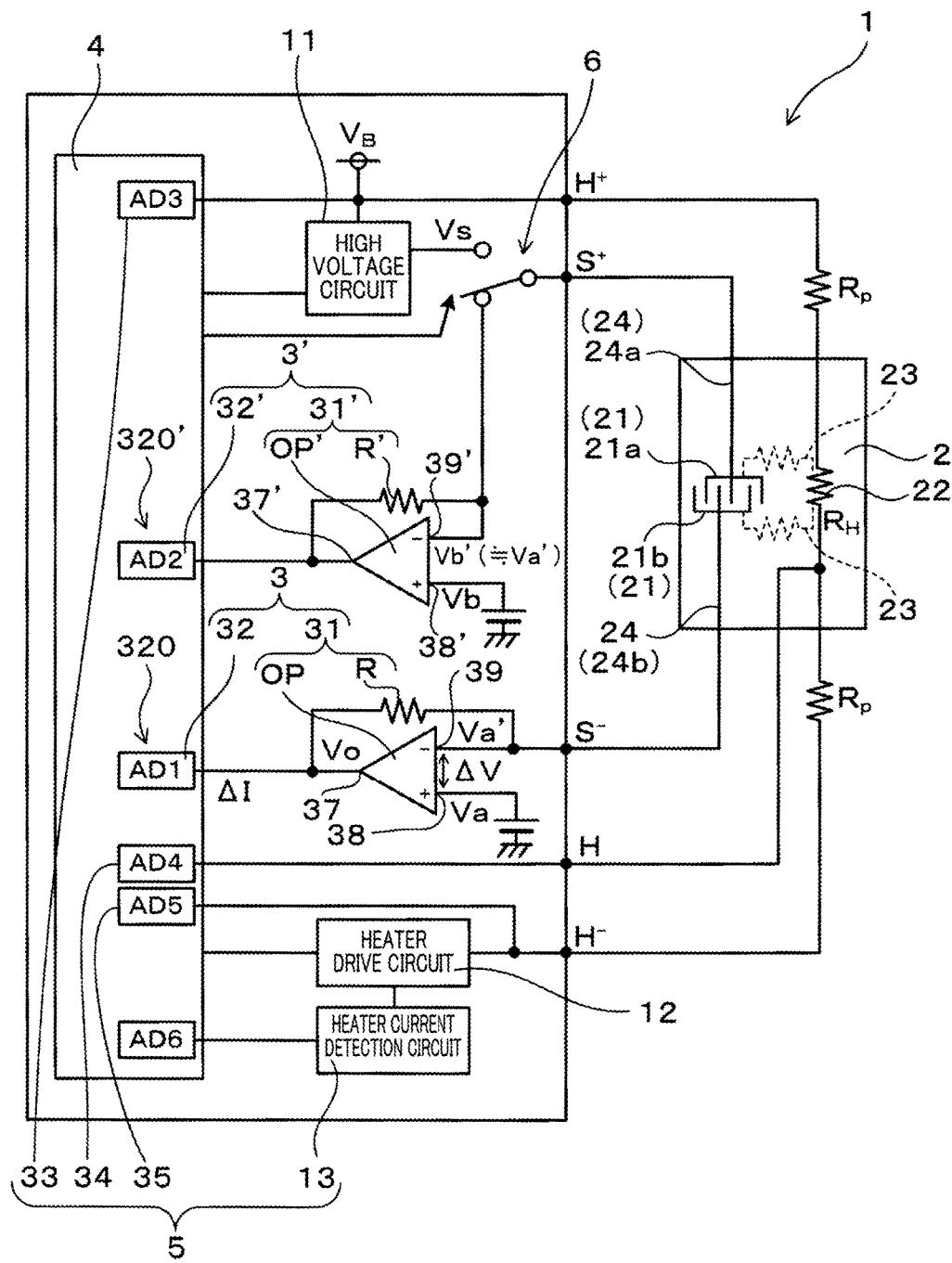
FIG. 1 is a view showing a circuit diagram of a particulate matter detection system according to a first exemplary embodiment of the present invention, and also showing a state of detecting an offset value of a current detection part.

The electrode 21 has a first electrode 21a and a second electrode 21b. As shown in FIG. 1, the current detection part 3 is connected to the second electrode 21b. The first electrode 21a is connected to an auxiliary current detection part 3' which will be explained later. The control circuit part 4 is connected to the particulate matter detection sensor 2 and the current detection part 3.

Figure 2:
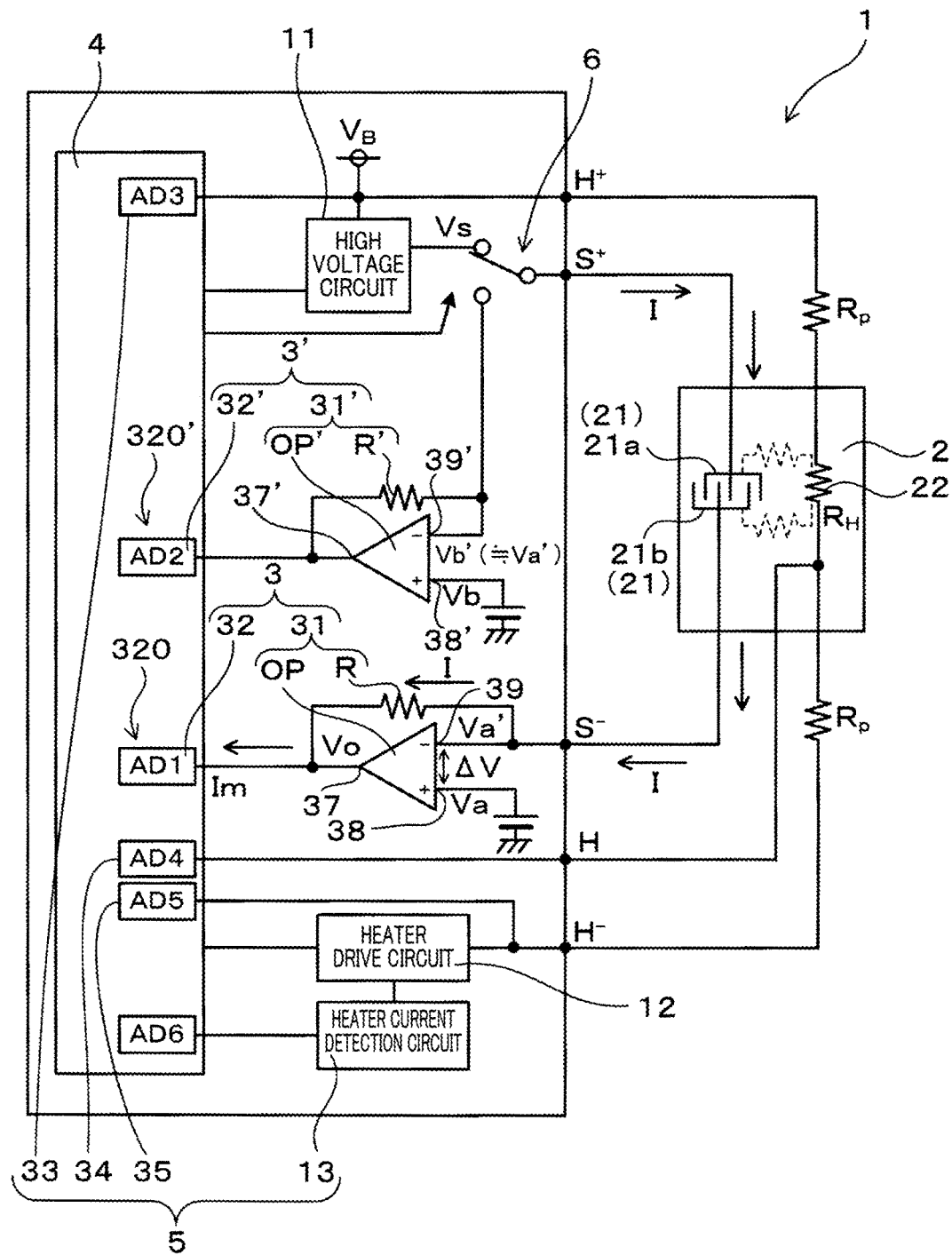
FIG. 2 is a view showing the circuit diagram of the particulate matter detection system in the detection mode according to the first exemplary embodiment of the present invention.
Figure 3:
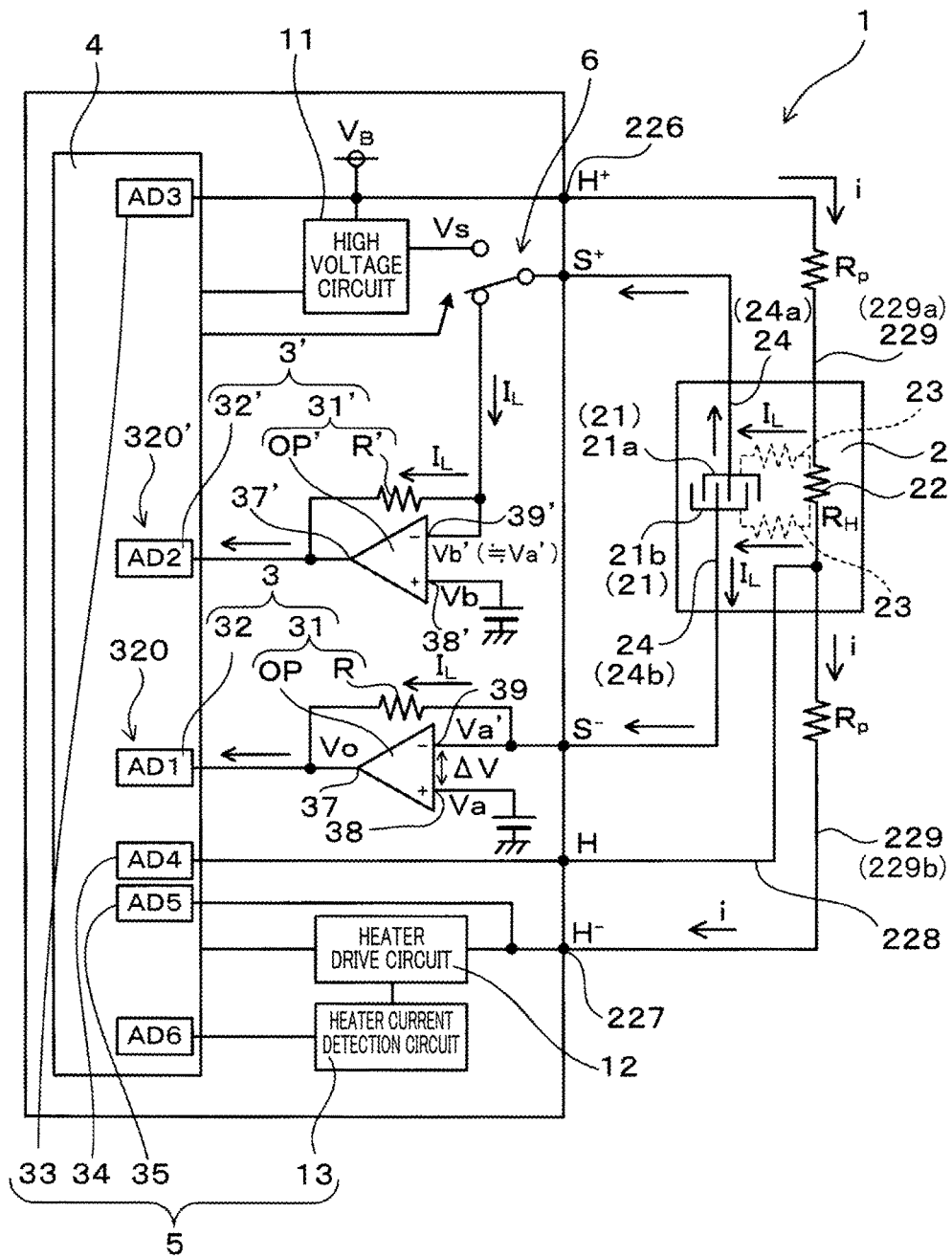
FIG. 3 is a view showing the circuit diagram of the particulate matter detection system in a burning mode according to the first exemplary embodiment of the present invention.

The control circuit part 4 performs the switching operation of the detection mode (see FIG. 2) and the burning mode (see FIG. 3). In the detection mode, the control circuit part 4 prohibits supply of power to the heater part 22, and a voltage is supplied between the pair of electrodes 21, and the current detection part 3 detects a current value flowing between the pair of electrodes 21. In the burning mode, electric power is supplied to the heater part 22 so as to burn particulate matter accumulated on the accumulation part 20.

As shown in FIG. 1, the control circuit part 4 supplies a voltage, which is lower than the voltage to be supplied to the pair of electrode 21 in the detection mode, at the time when the burning mode is switched to the detection mode, and the current detection part 3 detects a current flowing between the pair of electrodes 21. In this state, the control circuit part 4 receives the output value of the current detection part 3 as an offset value ΔI (see FIG. 8) which is a difference between a detected current value Im which is detected by the current detection part 3 and a true current value I. In the detection mode, the control circuit part 4 subtracts the offset value ΔI from the detected current value Im so as to correct the detected current value Im.

The particulate matter detection system 1 according to the first exemplary embodiment is mounted on a diesel vehicle. The control circuit part 4 is composed of a microcomputer system. The particulate matter detection system 1 according to the first exemplary embodiment is equipped with the auxiliary current detection part 3, a high voltage circuit 11, a switch 6, a heater drive circuit 12 and a heater current detection circuit 13.

As shown in FIG. 2, in the detection mode, the control circuit part 4 instructs the switch 6 to connect the first electrode 21a to the high voltage circuit 11. This makes it possible to supply a voltage between the first electrode 21a and the second electrode 21b, and to generate electromagnetic force so as to attract particulate matter contained in exhaust gas. For example, when particulate matter is accumulated on the accumulation part 20 (see FIG. 4), a current flows between the first electrode 21a and the second electrode 21b. The current detection part 3 detects this current, and the control circuit part 4 calculates an amount of particulate matter contained in exhaust gas on the basis of the detected current value.

When particulate matter accumulated on the accumulation part 20 increases, the current value detected by the current detection part 3 becomes saturated. In this case, the control circuit part 4 switches from the detection mode to the burning mode (see FIG. 3), and heats the heater part 22 so as to burn particulate matter accumulated on the accumulation part 20, and remove the particulate matter accumulated on the accumulation part 20 from the accumulation part 20.

The control circuit part 4 detects the offset value ΔI before the detection mode starts after the finish of the burning mode (see FIG. 1). As shown in FIG. 8, there is the following relationship between the true current value I, i.e. the true current value I, the detected current value Im detected by the current detection part 3 and the offset value ΔI: Im=I+ΔI.

That is, it is possible to obtain the equation of I=Im−ΔI on the basis of the relationship previously described. That is, it is possible to obtain the true current value I when the offset value ΔI is accurately obtained and this offset value ΔI is subtracted from the detected current value Im. This makes it possible to detect the amount of particulate matter contained in exhaust gas with high accuracy.

A description will be given of the method of detecting a current. As shown in FIG. 2, the current detection part 3 is equipped with a current voltage conversion circuit 31 and a voltage detection circuit 32. The current voltage conversion circuit 31 has an operational amplifier OP and a resistance which is arranged between an inverting input terminal 39 and an output terminal 37 of the operational amplifier OR The voltage detection circuit 32 is composed of a first A/D converter 320. The auxiliary current detection part 3' has a structure similar to the structure of the voltage detection circuit 32.

A non-inverting input terminal 38 of the operational amplifier OP is maintained at a predetermined voltage (hereinafter, also referred to as the non-inverting input terminal voltage Va). The inverting input terminal voltage Va' becomes substantially equal to the non-inverting input terminal voltage Va by virtual short-circuit as the characteristics of the operational amplifier OP. An input offset value ΔV is generated between the non-inverting input terminal 38 and the inverting input terminal 39. There is a relationship of Va'=Va−ΔV between the two input terminal voltages, i.e. the non-inverting input terminal voltage Va and the inverting input terminal voltage Va, and the offset voltage ΔV.

When particulate matter is accumulated in the particulate matter detection sensor 2, a current flows between the first electrode 21a and the second electrode 21b. The current does not flow into the inverting input terminal 39 of the operational amplifier OP, but flows through the resistance R. At this time, a voltage at the resistance R reduces by R×I. Accordingly, it is possible to express the output voltage Vo of the resistance R by the equation Vo=Va'−RI=Va−ΔV−RI.

When the equation previously described is converted, it can be recognized to express the true current I by using the following equation (2).

$$I = (Va - \Delta V - Vo)/R$$
$$= (Va - Vo)/R - \Delta V/R \ldots (2),$$
$$= Im - \Delta V \ldots (1),$$

where $Im = (Va - Vo)/R$, $\Delta I = \Delta V/R$.

The control circuit part 4 stores the values of the non-inverting input terminal voltage Va and the inverting input terminal voltage Va'. The control circuit part 4 is configured to calculate the detected current value Im on the basis of the output voltage Vo. However, because the input offset value $\Delta V$ is generated in the operational amplifier OP, the offset value $\Delta I$ is generated due to the input offset value $\Delta V$. Because the offset value $\Delta I$ varies due to a temperature, etc. Accordingly, the control circuit part 4 in the particulate matter detection system 1 according to the first exemplary embodiment periodically and accurately detects the offset value $\Delta I$, and calculates the true current value I by using the equation (1).

Next, a description will be given of the method of detecting the offset value $\Delta I$. As shown in FIG. 1, in the particulate matter detection system 1 according to the first exemplary embodiment, the control circuit part 4 instructs the switch 6 to connect the first electrode 21a to the auxiliary current detection part 3' when the burning mode is switched to the detection mode. The inverting input terminal voltage Va' of the operational amplifier OP, which forms the auxiliary current detection part 3', is substantially equal to the inverting input terminal voltage Va' of the operational amplifier OP which forms the current detection part 3. Accordingly, a voltage between the first electrode 21a and the second electrode 21b becomes substantially zero. This state prohibits a current from flowing between the first electrode 21a and the second electrode 21b even if some particulate matter are remained between the first electrode 21a and the second electrode 21b due to insufficient burning. Accordingly, the detected current value detected by the current detection part 3 becomes substantially equal to the input offset value $\Delta V$ (see FIG. 8). The control circuit part 4 accurately obtains the offset value $\Delta I$, and stores the obtained offset value $\Delta I$ therein. Through the description, the burning mode will also be called as "a regeneration mode" because the particulate matter detection sensor is regenerated in the regeneration mode.

On the other hand, as shown in FIG. 3, the particulate matter detection system 1 according to the first exemplary embodiment has a temperature detection part 5 capable of detecting a temperature of the heater part 22. The temperature detection part 5 has three A/D converters 33 to 35 and a heater current detection part 13. The temperature detection part 5 detects a heater resistance $R_H$ as an electrical resistance of the heater part 22, and calculates a temperature of the heater part 22 on the basis of the detected heater resistance $R_H$.

Figure 7:
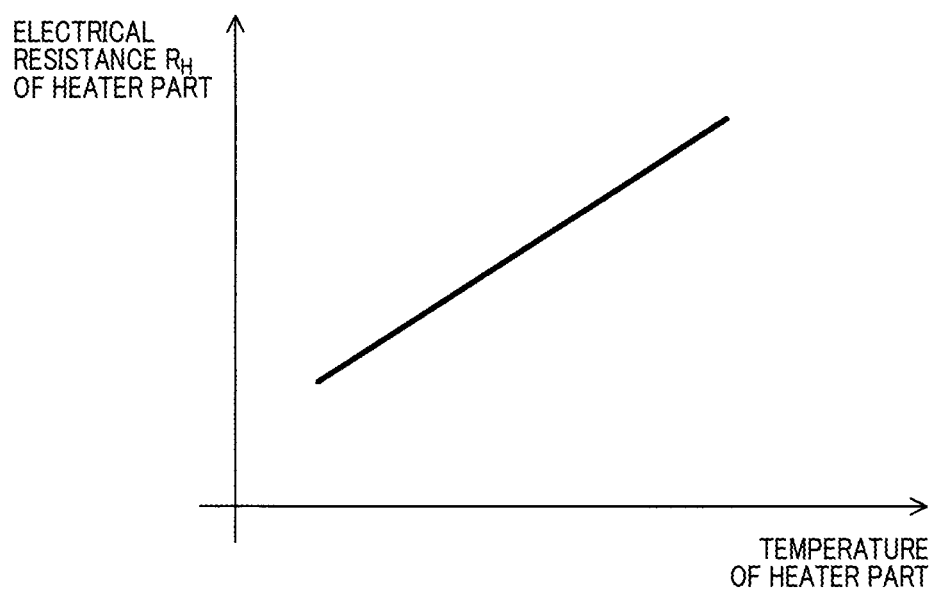
FIG. 7 is a graph showing a relationship between a temperature of the heater part and an electric resistance in the particulate matter detection system according to the first exemplary embodiment of the present invention.

As shown in FIG. 7, there is a constant relationship between the temperature of the heater part 22 and the heater resistance $R_H$. Accordingly, it is possible to calculate the temperature of the heater part 22 on the basis of the detected heater resistance $R_H$.

A description will now be given of detailed explanation of the method of detecting the temperature of the heater part 22. As shown in FIG. 3, because two heater wirings 229a and 229b have the same length, the heater wiring 229a and the heater wiring 229b have the same parasitic resistance Rp, respectively. The control circuit part 4 in the particulate matter detection system 1 according to the first exemplary embodiment detects a voltage $V_H$ between the terminals 226 and 227 connected to the heater wiring 229 by using a third A/D converter 33 and a fifth A/D converter 35. Further, the control circuit part 4 detects the current i which flows in the heater part 22 by using the heater current detection part 13. Further, the control circuit part 4 detects a total resistance Ra which is a sum of the heater resistance $R_H$ and the two wiring resistances Rp on the basis of the detected voltage $V_H$ and the detected current i. It is possible to express the total resistance Ra by using the following equation (3).

$$Ra = V_H/i = R_H + 2Rp \quad (3).$$

In the particulate matter detection system 1 according to the first exemplary embodiment, the control circuit part 4 detects the voltage Vp by using the fourth A/D converter 34 and the fifth A/D converter 35. This voltage Vp is supplied to the wiring resistance Rp as the parasitic resistance of the heater wiring 229b which is one of the heater wiring 229a and the heater wiring 229b. The control circuit part 4 uses the following equation (4) so as to calculate the wiring resistance Rp as the parasitic resistance of the heater wiring 229b.

$$Rp = Vp/i \quad (4).$$

For example, as shown in FIG. 3, the fourth A/D converter 34 is connected to a sensing wiring 228. This sensing wiring 228 is connected close to the heater part 22. The fourth A/D converter 34 in the control circuit part 4 detects the voltage Vp supplied to the heater wiring 229b through this sensing wiring 228. Although the sensing wiring 228 has a parasitic resistance, no current flows in the sensing wiring 228. Accordingly, because a very small voltage drop is generated in the sensing wiring 228, the control circuit part 4 detects the accurate voltage value Vp.

In the particulate matter detection system 1 according to the first exemplary embodiment, the temperature detection part 5 detects the total resistance Ra and the wiring resistance Rp by using the equations (3) and (4), and calculates the heater resistance value $R_H$ by using the equation of $R_H = Ra - 2R_P$. That is, the control circuit part 4 subtracts the two wiring resistance values Rp from the total resistance value Rp. This calculation makes it possible to calculate the accurate resistance value $R_H$ without influence from the wiring resistance value Rp, and to calculate the accurate temperature of the heater part 22.

Next, a description will be given of the action of the control circuit part 4 in the particulate matter detection system 1 according to the first exemplary embodiment with reference to the flowchart shown in FIG. 5.

Figure 5:
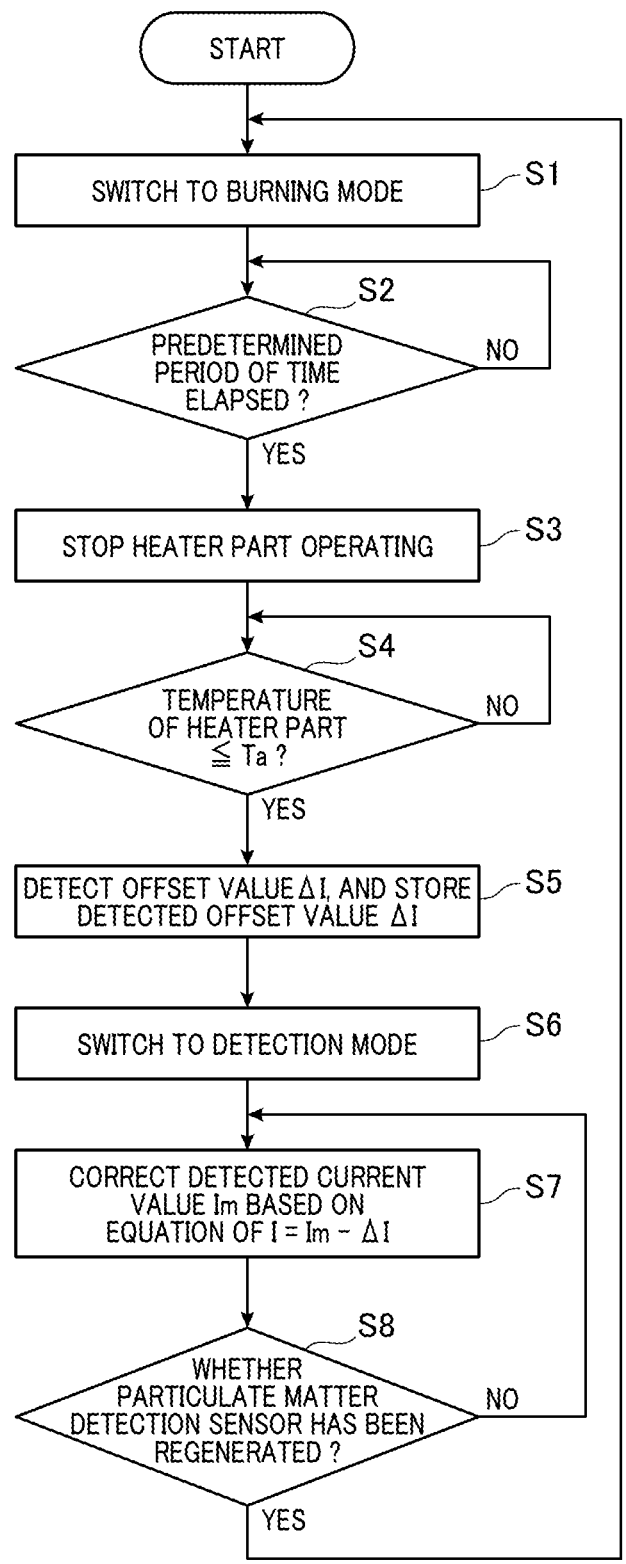
FIG. 5 is a flow chart showing an action of a control circuit part in the particulate matter detection system according to the first exemplary embodiment of the present invention.

As shown in FIG. 5, the control circuit part 4 enters the particulate matter detection system 1 into the burning mode in step S1.

Next, the operation flow progresses to step S2. In step 2, the control circuit part 4 detects whether a predetermined period of time has been elapsed. When the detection results indicates that the predetermined period of time has been elapsed, the operation flow progresses to step S3. In step S3, the control circuit part 4 prohibits supplying of power to the heater part 22. The operation flow progresses to step S4.

In step S4, the control circuit part 4 detects whether a temperature of the heater part 22 is lower than a predetermined lower limit value Ta. When the detection result indicates that the temperature of the heater part 22 is lower than the predetermined lower limit value Ta, i.e. the heater part 22 has been adequately cooled, the operation flow progresses to step S5.

In step S5, the control circuit part 4 detects the offset value $\Delta I$ of the current detection part 3, and stores it therein. That is, the control circuit part 4 performs the control of the switch 6 (see FIG. 1) so as to connect the first electrode 21a to the auxiliary current detection part 3'. This control operation provides a voltage between the pair of the first electrode 21a and the second electrode 21b which is substantially equal to zero, and prohibits the current from flowing between the first electrode 21a and the second electrode 21b even if some particulate matter remains due to insufficient burning. The control circuit part 4 detects, as the offset value ΔI, the current value Im output from the current detection part 3.

The operation flow progresses to step S6. In step S6, the control circuit part 4 allows the particulate matter detection system 1 to change from the burning mode into the detection mode. In the detection mode, the control circuit part 4 prohibits supply of power to the heater part 22, and instructs the switch 6 (see FIG. 2) to connect the first electrode 21a to the high voltage circuit 11. This control allows the voltage Vs of the high voltage circuit 11 to be supplied to the connection node between the electrodes 21. The voltage Vs is within a range of approximately 30 to 50 V. This control generates an electromagnetic field between the electrodes 21 and attracts particulate matter contained in exhaust gas by the generated electromagnetic field. Accordingly, a current flows between the electrodes 21 by the accumulation of the attracted particulate matter between the electrodes 21. The operation flow progresses to step S7. In step S7, the current detection part 3 detects this current which flows between the electrodes 21. As previously described, because the detected current value Im is shifted from the true current value I by the offset value ΔI, the control circuit part 4 corrects the detected current value Im by using the equation (1) (Step S7). The control circuit part 4 calculates the true current value I, and obtains a correct amount of particulate matter contained in exhaust gas on the basis of the calculated true current value I.

As shown in FIG. 5, the operation flow progresses to step 8 from step S7. In step S8, the control circuit part 4 determines whether to perform regeneration of the particulate matter detection sensor 2 on the basis of whether the current value I has been saturated. It is also acceptable for the control circuit part 4 to determine whether the predetermined period of time has been elapsed. When the determination result in step S8 indicates YES, the operation flow returns to step S1.

Next, a description will be given of the explanation of the graph which shows the relationship between the temperature of the heater part 22, the voltage of each of the first electrode 21a and the second electrode 21b, and the detected current value Im obtained by the current detection part 3 with reference to FIG. 6 (a) to (d).

Figure 6:
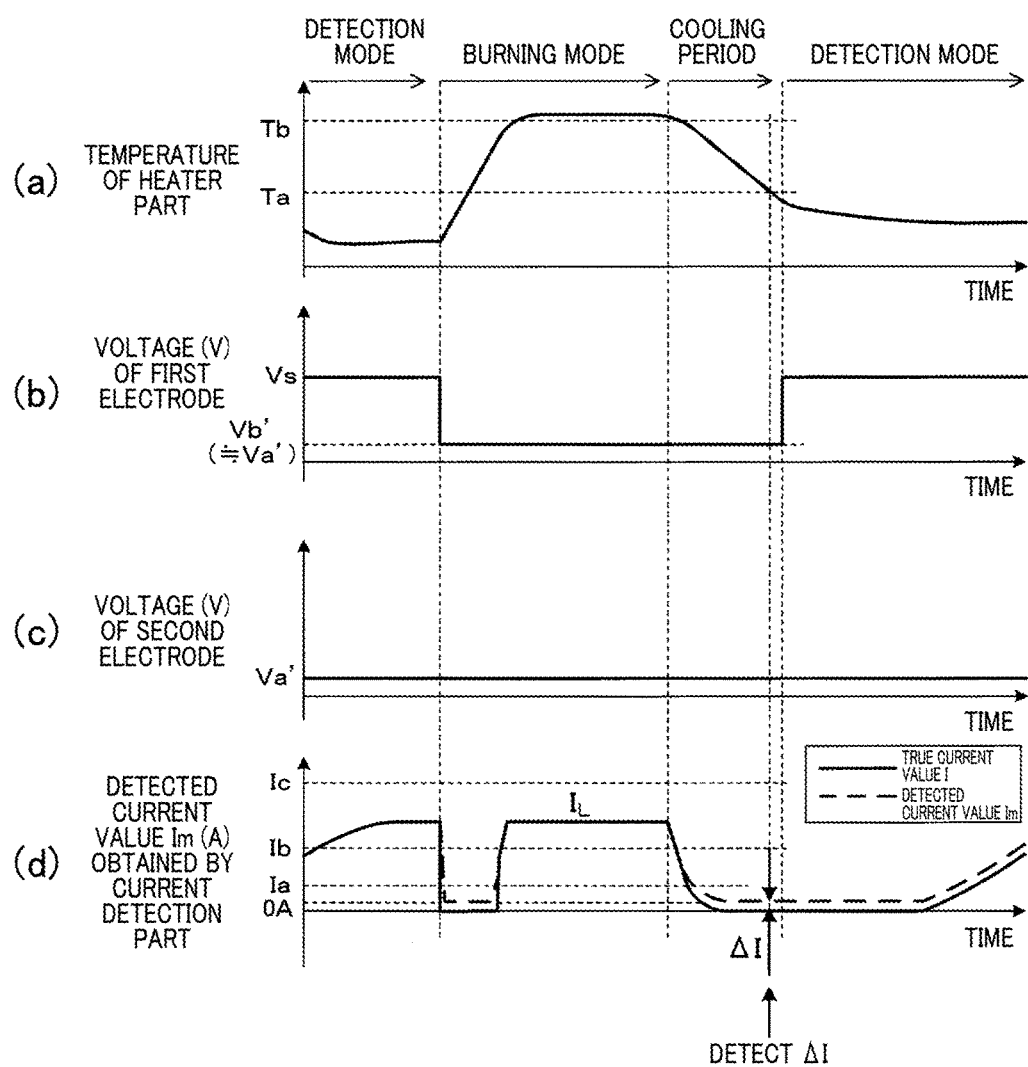
FIG. 6 is a diagram showing various graphs, (a) is a graph showing a temperature of a heater part, (b) is a graph showing a voltage potential of a first electrode, (c) is a graph showing a voltage potential of a second electrode, and (d) is a graph showing a time change of a current value detected by a current detection part in the particulate matter detection system according to the first exemplary embodiment of the present invention.

As shown in FIG. 6 (a), the temperature of the heater part 22 is relatively low in the detection mode. In the detection mode shown in FIG. 2, because the first electrode 21a is connected to the high voltage circuit 11, the first electrode 21a has the voltage Vs shown in FIG. 6 (b).

Because the second electrode 21b is connected to the inverting input terminal 39 of the operational amplifier OP, the voltage of the second electrode 21b is substantially equal to the inverting input terminal voltage Va, as shown in FIG. 6 (c).

Because particulate matter is accumulated between the first electrode 21a and the second electrode 21b after the detection mode is continued for a while, a current flows between the first electrode 21a and the second electrode 21b. As shown in FIG. 6 8d), the detected current value obtained by the current detection part 3 gradually increases.

When the detection mode is switched to the burning mode, the heater part 22 generates heat energy and a temperature of the heater part 22 increases. In the burning mode, because the first electrode 21a is connected to the auxiliary current detection part 3', the voltage at the first electrode 21a becomes equal to the inverting input terminal voltage Va' of the auxiliary current detection part 3'. Because the resistance value of the insulation member 23 (see FIG. 4) is reduced when the temperature of the heater part 22 adequately increases, a leak current $I_L$ flows from the heater part 22 to the first electrode 21a and the second electrode 21b. The current detection part 3 detects this current.

When the heater part 22 stops operating, the temperature of the heater part 22 gradually reduces. In the first exemplary embodiment, the control circuit part 4 detects the offset value ΔI after the temperature of the heater part 22 is lower than the predetermined lower limit value Ta, and the leak current value IL is adequately reduced.

Next, a description will be given of the action and effects of the particulate matter detection system 1 according to the first exemplary embodiment.

As shown in FIG. 5 and FIG. 6 (a) to (d), when the burning mode is switched to the detection mode, the control circuit part 4 is configured to supply the voltage to the pair of the electrodes 21, which is lower than the usual voltage supplied in the detection mode, and to detect the output of the current detection part 3 as the offset value ΔI. Accordingly, even if some particulate matter have remained between the pair of the electrodes 21 due to insufficient burning, it is possible to prohibit a current from flowing between the pair of the electrodes 21 by supplying the voltage to the pair of the electrodes 21 when the burning mode is switched to the detection mode, which is lower than the usual voltage used in the detection mode. In this case, because the output of the current detection part 3 is substantially equal to the offset value ΔI, it is possible for the control circuit part 4 to accurately obtain the offset value ΔI on the basis of the output of the current detection part 3.

Accordingly, it is possible for the control circuit part 4 to obtain the true current value I, which does not contain the offset value ΔI, on the basis of the corrected current value Im by subtracting the obtained offset value ΔI from the current value Im detected by the current detection part 3. This makes it possible to calculate the amount of particulate matter contained in exhaust gas with high accuracy.

It is preferable for the control circuit part 4 to use a low voltage at which no current substantially flows between the pair of the first electrode 21a and the second electrode 21b when detecting the offset value ΔI. It is preferable to use this voltage of not more than 1 V, and more preferable to use this voltage of not more than 0.1 V.

As shown in FIG. 5, the control circuit part 4 in the particulate matter detection system 1 according to the first exemplary embodiment is configured to detect the offset value ΔI after the temperature of the heater part 22 detected by the temperature detection part 5 becomes less than the predetermined lower limit value Ta (step S4, step S5) after particulate matter has been burned by heat energy generated in the heater part 22 (step S1).

Accordingly, it is possible for the control circuit part 4 to detect the offset value ΔI after no current substantially flows due to the reduction of the temperature of the heater part 22. This makes it possible for the control circuit part 4 to accurately obtain the offset value ΔI. It is therefore possible for the control circuit part 4 to correct the detected current value Im and to calculate an amount of particulate matter contained in exhaust gas with high accuracy in the detection mode. It is preferable for the control circuit part 4 to use the predetermined lower limit value Ta of not more than 500° C. when the insulation member 23 is made of alumina.

As previously described, it is possible for the first exemplary embodiment to provide the particulate matter detection system 1 capable of more accurately detecting an amount of particulate matter contained in exhaust gas.

(Second Exemplary Embodiment)

A description will be given of the particulate matter detection system according to a second exemplary embodiment with reference to FIG. 9, etc.

The same reference numbers and characters between the second exemplary embodiment and the first exemplary embodiment indicate the same parts and components in the particulate matter detection system. The explanation of the same parts and components is omitted here for brevity.

The second exemplary embodiment provides a modification of the process in the flow chart shown in FIG. 5 performed by the control circuit part 4 in the first exemplary embodiment.

Figure 9:
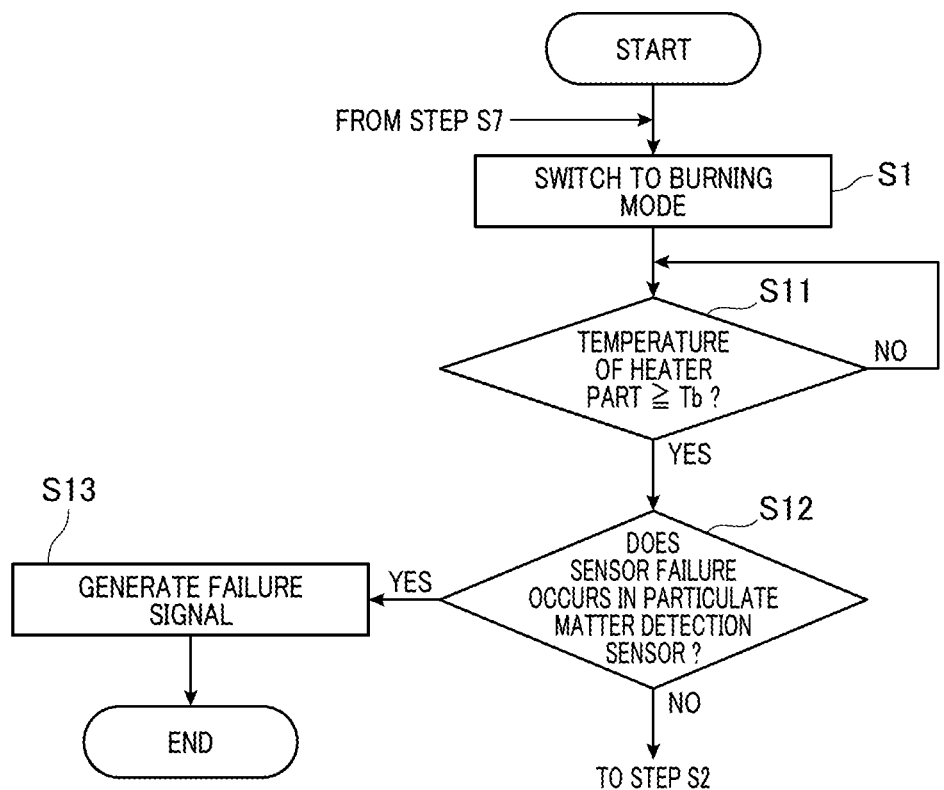
FIG. 9 is view showing a part of the flow chart of the control circuit part in the particulate matter detection system according to a second exemplary embodiment of the present invention.

In the second exemplary embodiment shown in FIG. 9, similar to the processes explained in the first exemplary embodiment, the operation flow progresses to step S11 after the process in step S1 has been finished. In step S11, the control circuit part 4 detects whether the temperature of the heater part 22 becomes not less than a predetermined temperature value Tb. When the detection result indicates YES, i.e. that the temperature of the heater part 22 becomes not less than the predetermined temperature value Tb, operation flow progresses to step S12. In step S12, the control circuit part 4 detects whether the particulate matter detection sensor 2 is in a malfunction situation. When the heater part 22 generates heat energy, the resistance value of the insulation member 23 reduces, and a leak current $I_L$ flows between the heater part 22 and the electrode 21 (see FIG. 6 (d)). In the second exemplary embodiment, the control circuit part 4 detects whether the particulate matter detection sensor 2 is in a malfunction situation on the basis of the detected leak current $I_L$.

As shown in FIG. 6 (b), when the particulate matter detection sensor 2 is correctly working, the current detection part 3 detects the leak current $I_L$ which is more than a predetermined current value Ib. On the other hand, when a line disconnection of a second wiring 24b occurs (see FIG. 3), no leak current $I_L$ flows, and the current detection part 3 does not detect the leak current $I_L$. Accordingly, it is possible for the control circuit part 4 to detect that a line disconnection of the second wiring 24b occurs when the leak current $I_L$ is less than a predetermined lower limit current value Ia (see FIG. 6 (b)). In this case, because the detection result in step S12 indicates YES, the operation flow progresses to step S13. In step S13, the control circuit part 4 generates a failure signal so as to inform the malfunction of the particulate matter detection sensor 2 to users.

In the particulate matter detection system 1 according to the second exemplary embodiment, the control circuit part 4 calculates the leak current $I_L$ on the basis of the equation of $I_L=Im-\Delta I$ in step S12. Accordingly, it is possible for the control circuit part 4 to detect the leak current $I_L$ with high accuracy without influence of the offset value $\Delta I$, and to perform the failure detection of the particulate matter detection sensor 2 with high accuracy.

In step S12 shown in FIG. 9, it is acceptable for the control circuit part 4 to detect whether the particulate matter detection sensor 2 is in a malfunction situation on the basis of the leak current $I_L$ detected by the auxiliary current detection part 3' in addition to the detection result of the current detection part 3.

Further, in step S12, it is possible for the control circuit part 4 to determine that a line disconnection occurs in the heater part 22 and the heater part 22 is not adequately heated when each of the leak current $I_L$ detected by the current detection part 3 and the leak current $I_L$ detected by the auxiliary current detection part 3' is less than the predetermined lower limit current value Ia.

Still further, it is acceptable for the control circuit part 4 to judge that deterioration has occurred in the insulation member 23, and the heater part 22 is in a malfunction when each of the leak current $I_L$ detected by the current detection part 3 and the leak current $I_L$ detected by the auxiliary current detection part 3' exceeds a predetermined upper limit current value Ic (see FIG. 6 (d)).

In addition, it is acceptable for the control circuit part 4 to provide detailed information regarding a failure part in the particulate matter detection sensor 2 instead of providing simple information which indicate only the occurrence of malfunction of the particulate matter detection sensor 2. The processes after step S12 are the same as the processes which have been explained in the first exemplary embodiment. The particulate matter detection system according to the second exemplary embodiment has the same structure, action and effects as the particulate matter detection system 1 according to the first exemplary embodiment.

(Third Exemplary Embodiment)

A description will be given of the particulate matter detection system according to a third exemplary embodiment with reference to FIG. 10, etc.

The third exemplary embodiment provides a modification of the circuit structure of the particulate matter detection system 1.

Figure 10:
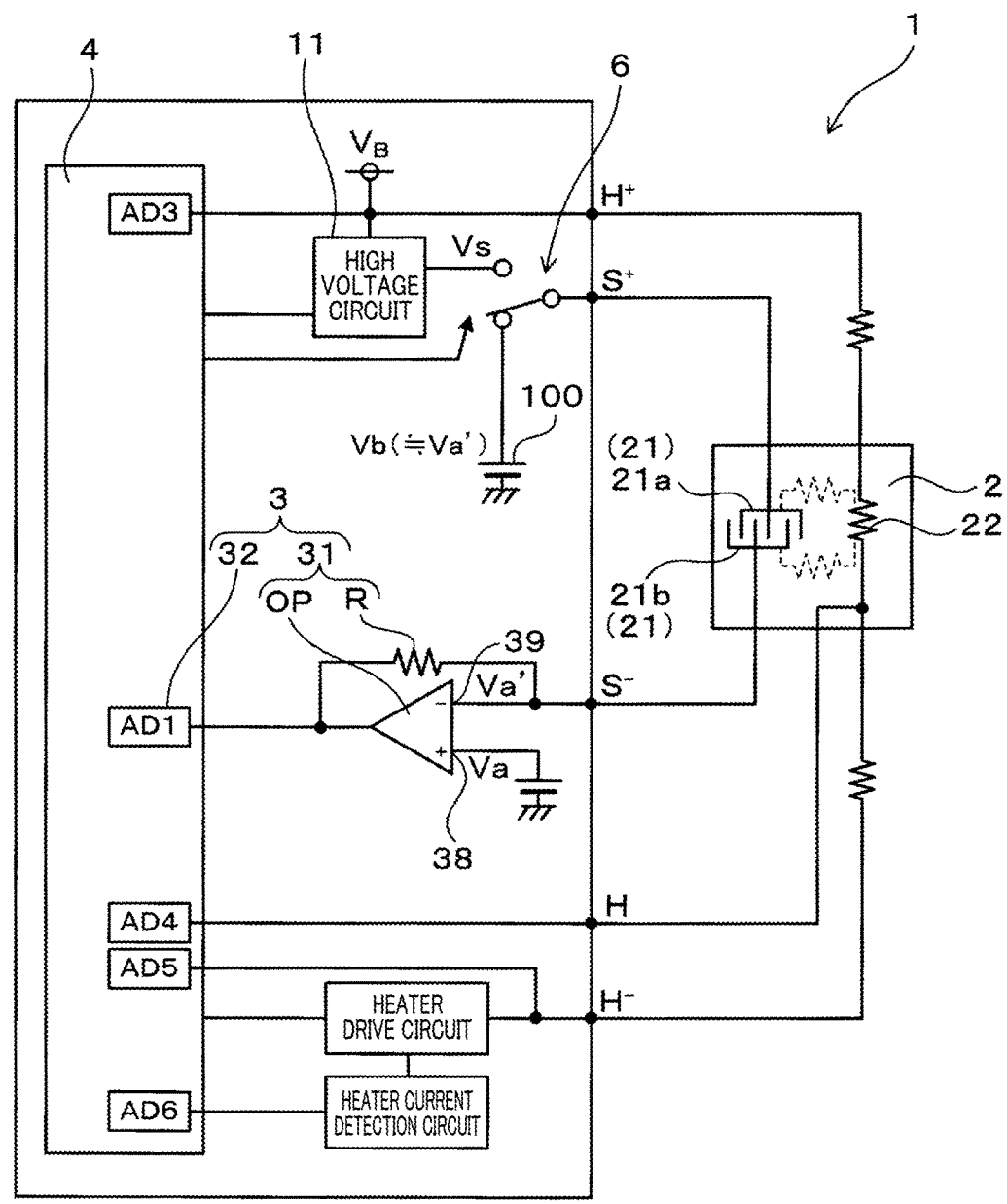
FIG. 10 is a view showing a state of detecting an offset value of the current detection part in the particulate matter detection system according to a third exemplary embodiment of the present invention.

As shown in FIG. 10, the particulate matter detection system according to the third exemplary embodiment has a voltage generation part 100, and does not have the auxiliary current detection part 3'.

A voltage Vb of the voltage generation part 100 is substantially equal to the inverting input terminal voltage Va' of the current detection part 3. The control circuit part 4 is configured to instruct the switch 6 to connect the first electrode 21a to the voltage generation part 100 when detecting the offset value $\Delta I$.

The particulate matter detection system according to the second exemplary embodiment has the same structure, action and effects as the particulate matter detection system according to the first exemplary embodiment.

(Fourth Exemplary Embodiment)

A description will be given of the particulate matter detection system according to a fourth exemplary embodiment with reference to FIG. 11, etc.

The fourth exemplary embodiment provides a modification of the circuit structure of the particulate matter detection system 1.

Figure 11:
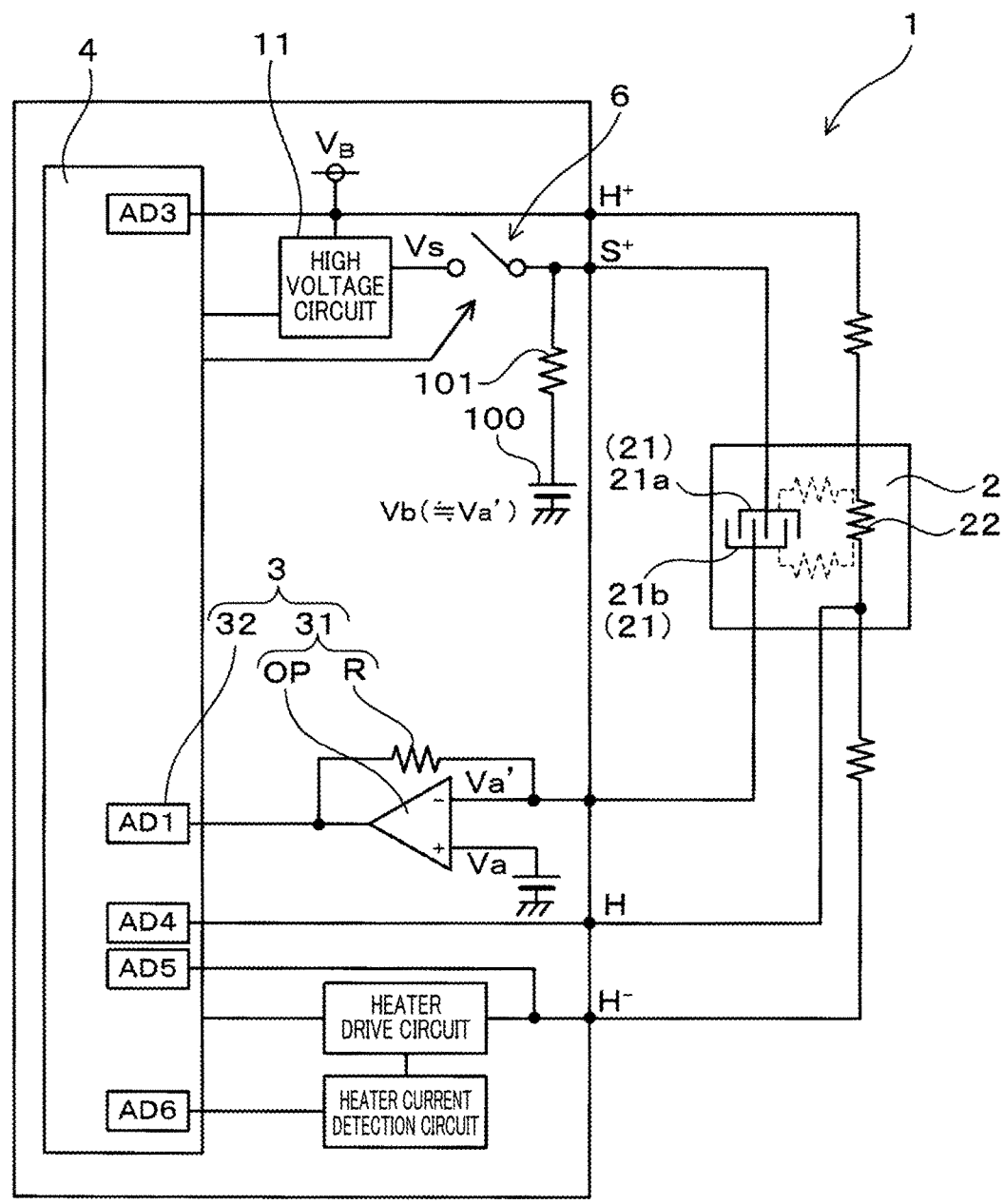
FIG. 11 is a view showing a state of detecting an offset value of the current detection part in the particulate matter detection system according to a fourth exemplary embodiment of the present invention.

As shown in FIG. 11, the particulate matter detection system according to the fourth exemplary embodiment has the voltage generation part 100, and does not have the auxiliary current detection part 3'. The voltage Vb of the voltage generation part 100 is substantially equal to the inverting input terminal voltage Va' of the current detection part 3. The voltage generation part 100 is always connected to the first electrode 21a through a resistance 101. In the detection mode, the control circuit part 4 in the particulate matter detection system according to the fourth exemplary embodiment is configured to turn ON the switch 6 to connect the first electrode 21a to the voltage generation part 100 when detecting the offset value $\Delta I$. This makes it possible to supply the voltage Vb of the voltage generation part 100 to the first electrode 21a.

The particulate matter detection system according to the fourth exemplary embodiment has the same structure, action and effects as the particulate matter detection system according to the first exemplary embodiment.

(Fifth Exemplary Embodiment)

Figure 12:
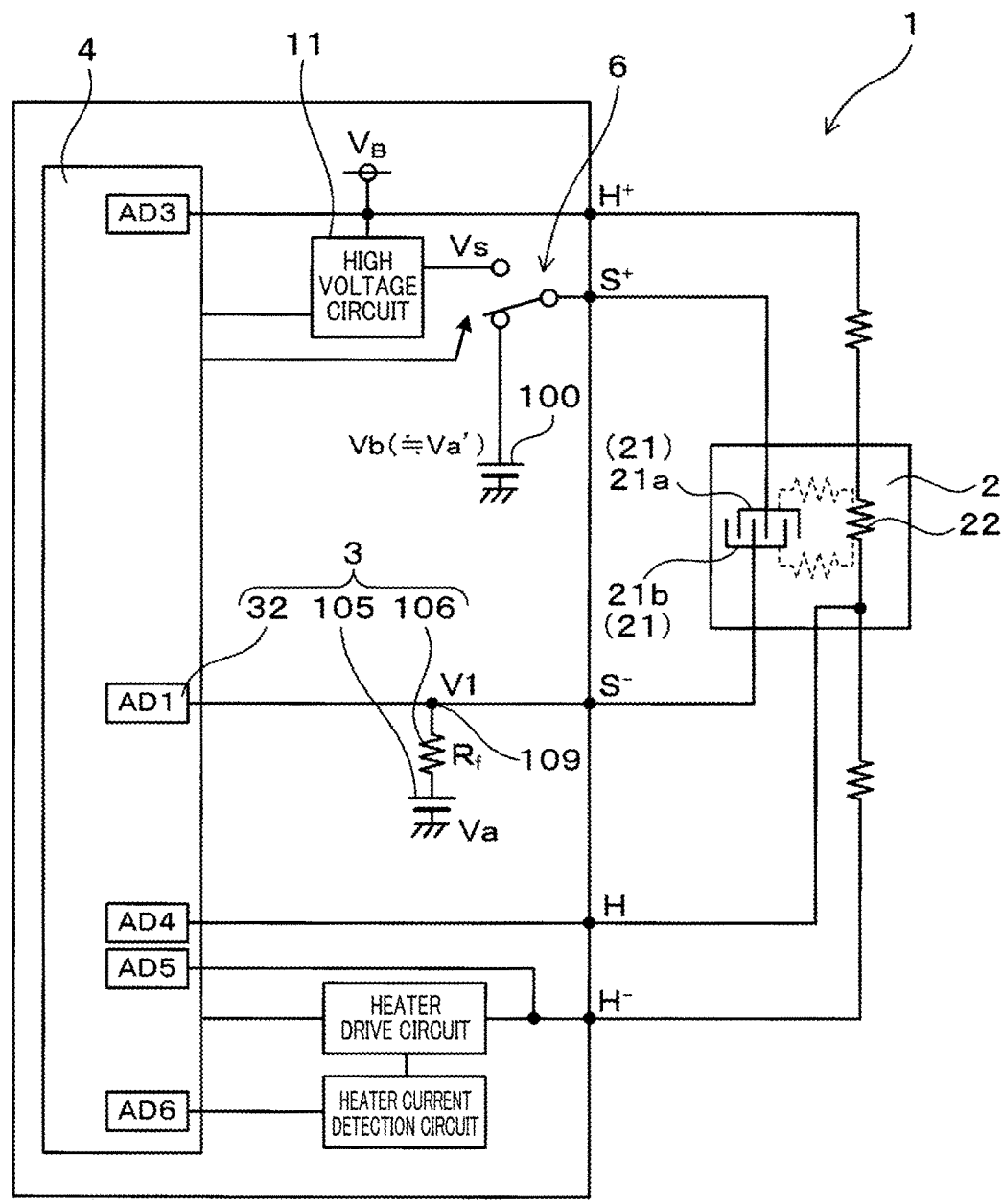
FIG. 12 is a view showing a state of detecting an offset value of the current detection part in the particulate matter detection system according to a fifth exemplary embodiment of the present invention.

A description will be given of the particulate matter detection system according to a fifth exemplary embodiment with reference to FIG. 12, etc.

The fifth exemplary embodiment provides a modification of the current detection part 3 in the particulate matter detection system. As shown in FIG. 12, the current detection part 3 in the particulate matter detection system according to the fifth exemplary embodiment is composed of the voltage detection circuit 32, a current limitation resistance 106, and a voltage generation part 105. The voltage detection circuit 32 detects a voltage at a connection node 109 between the current limitation resistance 106 and the second electrode 21b. The current detection part 3 is configured to detect a current which is flowing between the first electrode 21a and the second electrode 21b on the basis of the detected voltage at the connection node 109.

The particulate matter detection system according to the fifth exemplary embodiment has the same structure, action and effects as the particulate matter detection system according to the first exemplary embodiment.

(Sixth Exemplary Embodiment)

A description will be given of the particulate matter detection system according to a sixth exemplary embodiment with reference to FIG. 13, FIG. 14, etc. The sixth exemplary embodiment provides a modification of the flow chart shown in FIG. 4 performed by the control circuit part 4.

In the sixth exemplary embodiment, similar to the first exemplary embodiment, the control circuit part 4 performs processes of steps S1 to S6, step S7 and step S8. As shown in FIG. 13, after step S6, the operation flow progresses to step S61. In step S61, the control circuit part 4 detects whether the detected current value I immediately when the burning mode is switched to the detection mode is more than a predetermined current value Id. When some particulate matter remains between the first electrode 21a and the second electrode 21b due to insufficient burning, as shown in FIG. 14 (a) to (d), a current suddenly flows between the first electrode 21a and the second electrode 21b immediately when the burning mode is switched to the detection mode, and the current detection part 3 detects this current (see FIG. 14 (d)).

In step S61, the control circuit part 4 subtracts the offset value ΔI from the detected current value Im obtained by the current detection part 3, and calculates the true current value I on the basis of the subtraction. When the true current value I is more than the predetermined current value Id, the control circuit part 4 judges that some particulate matter has remained between the first electrode 21a and the second electrode 21b. The operation flow progresses to step S62. In step S62, the control circuit part 4 performs again the operation of the burning mode.

As shown in FIG. 13, the operation flow progresses to step S63 from step S62. In step S63, the control circuit part 4 detects whether the number of continuously-performed burning modes is a predetermined number N, i.e. detects that the particulate matter detection sensor 2 has been continuously regenerated N times?

When the detection result indicates No, the operation flow returns to step S6. On the other hand, the detection result indicates Yes, the operation flow progresses to step S64. In step S64, the control circuit part 4 judges and informs to the users that the particulate matter detection sensor 2 is in a malfunction situation and difficult to completely burn particulate matter, or non-burnable conductive material, i.e. particulate matter has still remained between the first electrode 21a and the second electrode 21b.

A description will be given of the action and effects as the particulate matter detection system according to the sixth exemplary embodiment. In the sixth exemplary embodiment, the control circuit part 4 is configured to judge that some particulate matter has remained between the first electrode 21a and the second electrode 21b when the current value I immediately when the burning mode is switched to the detection mode is more than the predetermined current value Id. In this case, the control circuit part 4 is further configured to perform the burning mode again (steps S61 and S62).

When the detection mode is continued under the situation in which some particulate matter has remained, due to insufficient burning, between the first electrode 21a and the second electrode 21b, it becomes difficult to detect a correct amount of particulate matter contained in exhaust gas. The particulate matter detection system according to the sixth exemplary embodiment having the improved structure previously described can avoid occurrence of the problem previously described because the burning mode is switched to the detection mode after particulate matter has been adequately burned.

Further, in the sixth exemplary embodiment, the control circuit part 4 subtracts the offset value ΔI from the detected current value Im obtained by the current detection part 3, and calculates the true current value I on the basis of the subtraction result in step S61. This makes it possible to calculate the true current value I without influence of the offset value ΔI. It is therefore possible for the control circuit part 4 to judge with high accuracy whether particulate matter has remained between the first electrode 21a and the second electrode 21b on the basis of the calculated true current value I.

In the sixth exemplary embodiment, the control circuit part 4 detects whether the number of continuously-performed burning modes is the predetermined number N (N times) (step S62). When the detection result indicates Yes, the control circuit part 4 judges and informs to the users that the particulate matter detection sensor 2 is in a malfunction situation (step S64). This makes it possible to prevent incorrect operation of the particulate matter detection system 1 under the heater part 22 is in a malfunction situation.

The particulate matter detection system according to the sixth exemplary embodiment has the same structure, action and effects as the particulate matter detection system according to the first exemplary embodiment.

REFERENCE SIGNS LIST

1 Particulate matter detection system, 2 Particulate matter detection sensor, 20 Accumulation part, 21 Electrodes, 22 Heater, 3 Current detection part, 4 Control circuit part, I Current value, Im Current detected value, and ΔI Offset value.

The invention claimed is:

1. A particulate matter detection system comprising:
   a particulate matter detection sensor;
   a current detection part; and
   a control circuit part,
wherein the particulate matter detection sensor comprises:
   an accumulation part on which particulate matter contained in exhaust gas is accumulated;
   a pair of electrodes arranged to be separated from each other on the accumulation part; and a heater part heating the accumulation part, and wherein the current detection part is electrically connected to one of the pair of electrodes, the control circuit part is electrically connected to the particulate matter detection sensor and the current detection part, the control circuit part performs switching of a detection mode and a burning mode, in the detection mode, the control circuit part prohibits supply of power to the heater part, supplies a voltage to the pair of electrodes, and instructs the current detection part to detect a current flowing between the pair of electrodes, and in the burning mode, the control circuit part instructs the heater part to generate heat energy so as to burn particulate matter accumulated between the pair of electrodes, during switching from the burning mode to the detection mode, the control circuit part supplies, to the pair of electrodes, a second voltage which is lower than a first voltage supplied between the pair of electrodes in the detection mode, and the control circuit part calculates, as an offset value ($\Delta I$), a difference between a true current value and a detected current value detected by the current detection part, and in the detection mode, the control circuit part subtracts the offset value ($\Delta I$) from the detected current value so as to correct the detected current value.

2. The particulate matter detection system according to claim 1, further comprising a temperature detection part detecting a temperature of the heater part, wherein the control circuit part is configured to calculate the offset value ($\Delta I$) after a temperature of the heater part detected by the temperature detection part becomes lower than a predetermined temperature value after the burning mode is finished.

3. The particulate matter detection system according to claim 1, the control circuit part is configured to perform the burning mode again so as to remove remaining particulate matter accumulated between the pair of electrodes when the corrected value of the detected current value is more than a predetermined current value immediately when the burning mode is switched to the detection mode.

4. The particulate matter detection system according to claim 1, the control circuit part supplies the voltage of not more than 1 V between the pair of electrodes in order to detect the offset value ($\Delta I$).

5. The particulate matter detection system according to claim 1, the control circuit part supplies the voltage of not more than 0.1 V between the pair of electrodes in order to detect the offset value ($\Delta I$).

* * * * *